United States Patent [19]

Grozil

[11] Patent Number: 5,074,375
[45] Date of Patent: Dec. 24, 1991

[54] HEARING PROTECTION SYSTEM ASSEMBLY

[76] Inventor: Richard S. Grozil, 635 Tie Chute La., Florence, Mont. 59833

[21] Appl. No.: 565,657

[22] Filed: Aug. 10, 1990

Related U.S. Application Data

[63] Continuation-in-part of Ser. No. 414,269, Oct. 18, 1989.

[51] Int. Cl.⁵ .......................... A61B 7/02; A61F 11/02
[52] U.S. Cl. ........................................ 181/135; 128/864
[58] Field of Search ............... 181/135, 130, 134, 129; 128/864, 152; 381/68, 68.6

[56] References Cited

U.S. PATENT DOCUMENTS

| | | | |
|---|---|---|---|
| D. 262,491 | 12/1981 | Ebert | D24/67 |
| 2,946,394 | 7/1960 | Smith | 181/135 |
| 3,800,791 | 4/1974 | Visor | 181/135 X |
| 4,314,553 | 2/1982 | Westerdal | 181/135 X |

*Primary Examiner*—Brian W. Brown
*Assistant Examiner*—Jae N. Noh
*Attorney, Agent, or Firm*—John R. Flanagan

[57] ABSTRACT

A hearing protection system includes a pair of assemblies each composed of an ear plug, ear plug retainer, and attachment member. The ear plug is a plastic foam body resiliently compressible for conforming to a user's ear canal. The body has an axial bore at its rear end and a conical exterior surface convergently tapering from rear to front end. Axially spaced outwardly projecting annular shoulders are formed about the conical exterior surface of the body for engaging the user's ear canal. The ear plug retainer has stem, stop and connecting portions rigidly interconnected from one to the next. The stem portion is an elongated shaft attached at one end to the stop portion and insertable at an opposite and into the bore in the ear plug body. The shaft has a plurality of axially spaced outwardly projecting annular ridges for providing an interference fit within the ear plug bore. The stop portion abuts the rear end of the ear plug for limiting insertion of the stem portion into the ear plug bore. The connecting portion projects from a side of the stop portion opposite from the side connected to the stem portion and contains an aperture. The attachment member is an elongated flexible strap having either identical or different attachment elements at its opposite ends with one element being attachable through the aperture of the ear plug retainer connecting portion.

20 Claims, 2 Drawing Sheets

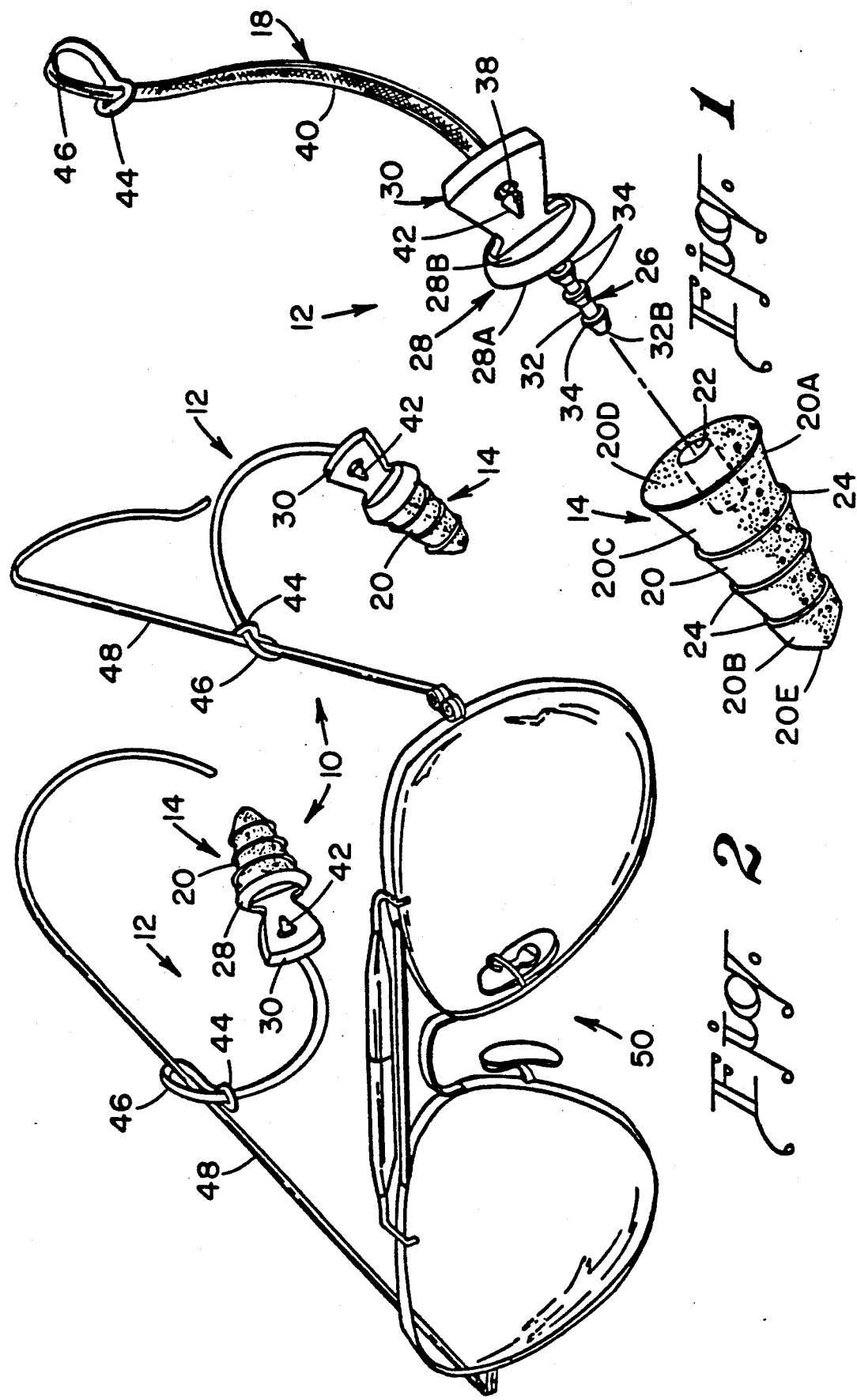

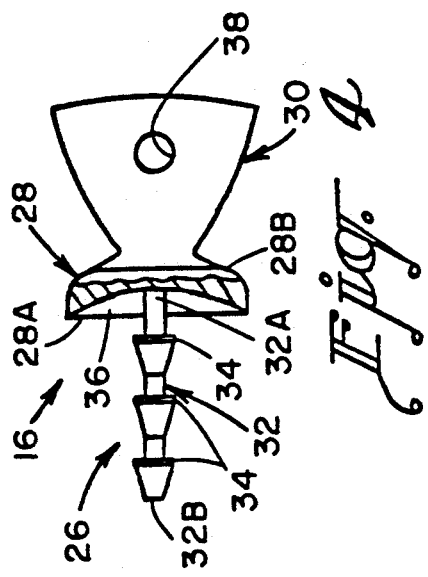
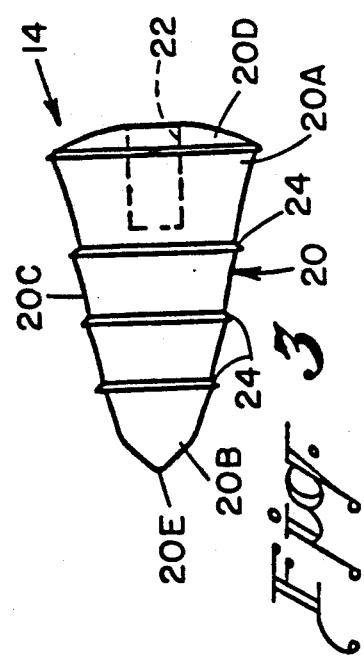
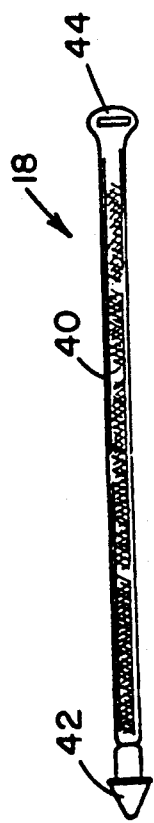
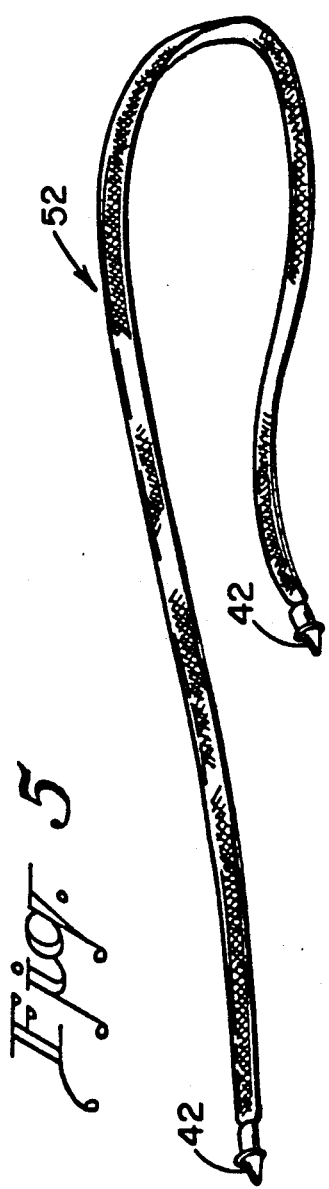

HEARING PROTECTION SYSTEM ASSEMBLY

CROSS REFERENCE TO RELATED APPLICATION

This application is a continuation-in-part of copending U.S. Pat. application Ser. No. 414,269, filed Oct. 18, 1989.

BACKGROUND OF THE INVENTION

1. Field of the Invention

The present invention generally relates to devices for protection of human hearing and, more particularly, is concerned with a versatile hearing protection system assembly for use by persons active in noise intensive environments.

2. Description of the Prior Art

Levels of noise potentially harmful to the human hearing system are common in a number of diverse settings, for example, work, home, and recreational environments. Several approaches have been proposed in the prior art to protect hearing by reducing the amount of noise reaching persons hearing systems.

One approach to noise reduction in the prior art is the provision of a headset having an expandable semi-circular band that fits over the top of a wearer's head and a pair of cup-shaped members mounted to the opposite ends of the band for covering the wearer's ears. The main drawbacks of the headset approach to noise reduction is high cost and user discomfort both of which are attributable to the size and weight of the headset and the total enclosure of the wearer's ears.

Another approach to noise reduction in the prior art is the provision of a pair of ear plugs which fit into the canals of a wearer's ears. The ear plugs are provided separately or with a cord for attaching them together. Examples of such approach are illustrated and described in German Patent Document No. DE 3304 362 A1 to Schleicher, U.S. Pat. No. 3,871,372 to Bivins and U.S. Pat. No. 4,314,553 to Westerdal.

The provision of ear plugs is believed to be the preferred one of the two cited approaches. However, none of the devices of the cited prior art patent references are felt to represent a particularly desirable nor highly satisfactory solution to the problem of how best to protect human hearing from high levels of environmental noise.

Consequently, a pressing need remains unfulfilled for an improved approach to hearing protection in noise intensive settings.

SUMMARY OF THE INVENTION

The present invention provides a hearing protection system assembly designed to satisfy the aforementioned need. The hearing protection system preferably includes a pair of the assemblies, one for each ear. The hearing protection system assemblies of the present invention meet the hearing protection requirements and needs of both industry (i.e. manufacturing, aerospace, automotive, military, etc.) and the general public (i.e., home workshop, lawn care, motor racing events, etc.).

The hearing protection system assembly of the present invention also gives users the option of how to wear the assemblies, for instance, by attachment to safety glasses or goggles as well as other eyewear such as shooting glasses and sun glasses, or by attachment together about the back of the user's neck. Further, the assembly is sanitary to use in that it permits replacement of the ear plug component which contacts the ear canal and allows cleaning and reuse of the other components.

Accordingly, the present invention is directed to a hearing protection system assembly which comprises an ear plug, ear plug retainer, and an attachment member.

The ear plug of the hearing protection assembly is a resiliently compressible body conformable to a user's ear canal. The body has rear and front ends, a bore formed in the rear end, and an exterior surface tapering convergently from the rear to front end.

The ear plug retainer of the hearing protection assembly is composed of stem, stop and connecting portions, being serially arranged and rigidly connected from one to the next. The stem portion of the ear plug retainer has an elongated shaft rigidly attached at one end to the stop portion and insertable at an opposite end into the rear end bore of the ear plug body. The stem portion also has at least one and preferably several annular ridges formed on the shaft spaced from one another between the opposite ends thereof. Each annular ridge projects outwardly from and about the shaft for providing an interference fit with the ear plug body upon insertion of the shaft into the ear plug bore.

The stop portion of the ear plug retainer has opposite sides and a larger diameter than the ear plug bore for abutting the rear end of the ear plug body to limit insertion of the stem portion shaft into the ear plug bore. The connecting portion of the ear plug retainer is rigidly attached to and projects from one of the sides of the stop portion being opposite from the side at which the stem portion is connected to the stop portion.

The attachment member of the hearing protection assembly is releasably fastenable to the connecting portion of the ear plug retainer. The attachment member is composed of an elongated flexible strap having first and second attachment elements at its opposite ends. At least one of the elements is detachably attachable to the connecting portion of the ear plug retainer.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which:

FIG. 1 is a partly exploded perspective view of one assembly of a hearing protection system in accordance with the present invention.

FIG. 2 is a perspective view of a pair of eyeglasses having a pair of assemblies of the hearing protection system of the present invention attached to the temple pieces of the eyeglasses.

FIG. 3 is an enlarged side elevational view of an ear plug of the hearing protection system assembly of FIG. 1.

FIG. 4 is an enlarged partly sectioned side elevational view of an ear plug retainer of the hearing protection system assembly of FIG. 1.

FIG. 5 is an enlarged side elevational view of an attachment member of the hearing protection system assembly of FIG. 1 being a lanyard particularly adapted for attachment to a temple piece of eyeglasses as shown in FIG. 2.

FIG. 6 is a perspective view of an alternate form of the attachment member of the hearing protection system assembly.

DETAILED DESCRIPTION OF THE INVENTION

Referring to the drawings, and particularly to FIGS. 1 and 2, there is shown a pair of assemblies 10 constituting a hearing protection system 12 in accordance with the present invention. In its basic components, each assembly 10 includes an ear plug 14, an ear plug retainer 16, and an attachment member 18. Each of the components can be manufactured from readily available plastic materials which, when assembled, provides the user with a comfortable, convenient hearing protection system that can be used with or without protective eyewear.

More particularly, referring to FIGS. 1-3, the ear plug 14 of the hearing protection assembly 10 is a resiliently compressible body 20 conformable to a user's ear canal. Preferably, the body 20 is disposable and composed of a mucus-tolerant plastic material, by way of example, such as dense polyurethane foam. The ear plug body 20 has rear and front ends 20A and 20B, a bore 22 formed in the rear end 20A, and a substantially conical exterior surface 20C which tapers convergently from the rear end 20A to the front end 20B of the body. The rear end 20A of the ear plug body 20 has a large rounded convex end surface 20D that surrounds the opening to the bore 22. The front end 20B of the body 20 has a small relatively blunt edge 20E.

Also, the ear plug body 20 has a plurality of axially spaced annular shoulders 24 formed thereon. The shoulders 24 generally face rearwardly and taper forwardly so as to facilitate insertion of the ear plug 20 while resisting its removal.

Referring to FIGS. 1, 2 and 4, the ear plug retainer 16 of the hearing protection assembly 10 is composed of stem, stop and connecting portions 26, 28 and 30, which are serially arranged and rigidly connected from one to the next. The retainer 16 can be injection molded from flexible polyproplene plastic as a one-piece structure.

The stem portion 26 of the ear plug retainer 16 has an elongated shaft 32 rigidly attached at one end 32A to the stop portion 28 and insertable at an opposite end 32B into the rear end bore 22 of the ear plug body 20. The stem portion 26 also has at least one and preferably several annular ridges 34 formed concentrically about the shaft 32 and axially spaced from one another between the opposite ends 32A and 32B of the shaft. Each annular ridge 34 projects outwardly from and about the shaft 32 for providing an interference fit with the ear plug body 20 upon insertion of the shaft 32 into the ear plug bore 20. Each ridge 34 further has a frusto-conical shape facing generally rearwardly toward the stop portion 28 and tapering forwardly so as to facilitate insertion of the retainer stem portion 26 into the ear plug body bore 22 while resisting its removal therefrom.

The stop portion 28 of the ear plug retainer 16 has opposite sides 28A and 28B and a larger diameter than the ear plug bore 22 for abutting the rear end 20A of the ear plug body 20 to limit insertion of the stem portion shaft 32 into the ear plug bore 22. The stop portion 28 at its front one side 28A has a concave surface 36 for receiving and cradling the convex rear end surface 20D of the ear plug body 20.

The connecting portion 30 of the ear plug retainer 16 is rigidly attached to and projects from the rear other side 28B of the stop portion 28 opposite from the front one side 28A where the stem portion 26 is connected to the stop portion 28. The connecting portion 30 is a tab having an aperture 38 through it.

Referring to FIGS. 1, 2 and 5, the attachment member 18 of the hearing protection assembly 10 is releasably fastenable to the connecting portion 30 of the ear plug retainer 16. The attachment member 18 is composed of an elongated flexible strap 40, such as a lanyard, having first and second attachment elements 42 and 44 at its opposite ends. The strap 40 can be injection-molded from PYC plastic. The first attachment element 42 is a compressible tapered round spear or nose capable of insertion through the aperture 38 of the tab 30 and thereby detachably attachable to the connecting portion 30 of the ear plug retainer 16. The second attachment element 44 is a flat slotted ring capable of receiving insertion of the tapered nose 42 therethrough for defining a loop 46 at one end of the attachment member 18 which can be installed over one of the temple pieces 48 of a pair of eyeglasses, as seen in FIG. 2.

Referring to FIG. 6, in an alternate form, the attachment members 18 of of the pair of assemblies are connected together and formed as a single lanyard 52. The attachment elements 42 on opposite ends thereof are substantially identical, each being the compressible tapered round spear or nose capable of insertion through the apertures 38 of the connecting portions 30 of the ear plug retainers 16.

It is thought that the present invention will be understood from the foregoing description and it will be apparent that various changes may be made thereto without departing from its spirit and scope or sacrificing all of its material advantages, the form hereinbefore described being merely preferred or exemplary embodiment thereof.

Having thus described the invention, what is claimed is:

1. An assembly for a hearing protection system, comprising:
   (a) an ear plug having a resiliently compressible body conformable to a user s ear canal, said body having rear and front ends, a bore formed in said rear end, and an exterior surface tapering convergently from said rear to front end;
   (b) an ear plug retainer composed of stem, stop and connecting portions serially arranged and rigidly connected from one to the next, said stem portion having an elongated shaft rigidly attached at one end to one side of said stop portion and insertable at an opposite end into said bore of said ear plug body, said stem portion also having at least one annular ridge formed on said shaft and projecting outwardly from and about said shaft for providing an interference fit with said ear plug body upon insertion of said shaft into said ear plug bore, said stop portion having a larger diameter than said ear plug bore for abutting said rear end of said ear plug body at said one side of said stop portion to limit insertion of said stem portion shaft into said ear plug bore, said connecting portion rigidly attached to and projecting from the other side of said stop portion opposite from said one side at which said stem portion is connected to said stop portion; and
   (c) an attachment member releasably fastenable to said connecting portion of said ear plug retainer and composed of an elongated flexible strap having first and second attachment elements at its opposite ends, at least one of said elements being detachably attachable to said connecting portion of said ear plug retainer.

2. The assembly of claim 1 wherein said ear plug body is of a mucus-tolerant plastic foam material.

3. The assembly of claim 1 wherein:
said rear end of said ear plug body has a rounded convex end surface surrounding said bore; and
said stop portion at said one side has a concave surface for receiving and cradling said convex end surface of said ear plug body.

4. The assembly of claim 1 wherein said stem portion of said ear plug retainer has a plurality of axially spaced annular ridges formed on said shaft.

5. The assembly of claim 1 wherein each of said ridges has a frusto-conical shape.

6. The assembly of claim 1 wherein said exterior surface on said ear plug body has a substantially conical shape.

7. The assembly of claim 1 wherein said ear plug body has a plurality of axially spaced annular shoulders formed thereon.

8. The assembly of claim 1 wherein said attachment member is a lanyard having identical attachment elements on opposite ends thereof.

9. The assembly of claim 1 wherein:
said connecting portion of said ear plug retainer has an aperture; and
said one of said attachment elements is a compressible tapered nose capable of insertion through said aperture of said connecting portion.

10. The assembly of claim 9 wherein said other of said attachment elements is a slotted ring capable of insertion of said tapered nose therethrough for defining a loop at one end of said attachment member.

11. A hearing protection system, comprising:
(a) a pair of assemblies each including an ear plug, an ear plug retainer, and an attachment member;
(b) said ear plug being composed of a body of a plastic foam material resiliently compressible for conforming to a user's ear canal, said body having rear and front opposite ends, a bore formed axially into said body from said rear end thereof and a substantially conical exterior surface convergently tapering from said rear to front end;
(c) said ear plug retainer being composed of stem, stop and connecting portions rigidly interconnected from one to the next, said stem portion having an elongated shaft attached at one end to one side of said stop portion and insertable at an opposite end into said bore of said ear plug body, said stem portion also having at least one annular ridge formed on said shaft and projecting outwardly from and about said shaft for providing an interference fit with said ear plug body upon insertion into said ear plug bore, said stop portion having a larger diameter than said ear plug bore and being capable of abutting said rear end of said ear plug body at said one side of said stop portion to limit insertion of said stem portion shaft into said ear plug bore, said connecting portion having a tab with an aperture therethrough, said tab rigidly attached to and projecting from the other side of said stop portion opposite from said one side at which said stem portion is connected to said stop portion;
(d) said attachment member being fastened to said tab of said connecting portion of said ear plug retainer and composed of an elongated flexible strap having first and second attachment elements at its opposite ends, at least one of said elements being attachable to said tab of said ear plug retainer.

12. The system of claim 11 wherein said rear end of said ear plug body has a rounded convex end surface surrounding said bore.

13. The system of claim 12 wherein said stop portion at said one side has a concave surface for receiving and cradling said convex end surface of said ear plug body.

14. The system of claim 11 wherein said stem portion of said ear plug retainer has a plurality of axially spaced annular ridges formed on said shaft.

15. The system of claim 14 wherein each of said ridges has a frusto-conical shape.

16. The system of claim 11 wherein said ear plug body has a plurality of axially spaced annular shoulders formed thereon.

17. The system of claim 11 wherein said attachment member is a lanyard having identical attachment elements on opposite ends thereof.

18. The system of claim 11 wherein said one of said attachment elements is a compressible tapered nose capable of insertion through said aperture of said connecting portion tab.

19. The system of claim 11 wherein said other of said attachment elements is a slotted ring capable of insertion of said tapered nose therethrough for defining a loop at one end of said attachment member.

20. The system of claim 11 wherein said attachment members of said pair of assemblies are connected together and said attachment elements on opposite ends thereof are substantially identical.

* * * * *